US00PP20415P2

(12) United States Plant Patent
Bergman

(10) Patent No.: US PP20,415 P2
(45) Date of Patent: Oct. 13, 2009

(54) ***HIBISCUS* PLANT NAMED 'RED NALU'**

(50) Latin Name: *Hibiscus rosa-sinensis*
Varietal Denomination: Red Nalu

(75) Inventor: Wendy R. Bergman, Lehigh Acres, FL (US)

(73) Assignee: Yoder Brothers, inc., Barberton, OH (US)

( * ) Notice: Subject to any disclaimer, the term of this patent is extended or adjusted under 35 U.S.C. 154(b) by 0 days.

(21) Appl. No.: 12/221,687

(22) Filed: Aug. 4, 2008

(51) Int. Cl.
*A01H 5/00* (2006.01)

(52) U.S. Cl. ..... Plt./257
(58) Field of Classification Search ..... Plt./257
See application file for complete search history.

*Primary Examiner*—Kent L Bell
(74) *Attorney, Agent, or Firm*—C. A. Whealy

(57) ABSTRACT

A new and distinct cultivar of *Hibiscus* plant named 'Red Nalu', characterized by its compact, upright, outwardly spreading and dense plant habit that is appropriate for container production; glossy dark green-colored leaves; uniform, freely and early flowering habit; large dark red-colored flowers with burgundy-colored centers; and good postproduction and garden performance.

1 Drawing Sheet

Botanical designation: *Hibiscus rosa-sinensis.*
Cultivar denomination: 'Red Nalu'.

BACKGROUND OF THE INVENTION

The present invention relates to a new and distinct cultivar of *Hibiscus,* botanically known as *Hibiscus rosa-sinensis,* and hereinafter referred to by the name 'Red Nalu'.

The new *Hibiscus* is a product of a planned breeding program conducted by the Inventor in Alva, Fla. The objective of the breeding program is to create new freely-branching *Hibiscus* cultivars with a dense, uniform and compact plant habit appropriate for container production, early and uniform flowering, numerous flowers per lateral branch, desirable flower color and good garden performance.

The new *Hibiscus* originated from a cross-pollination made by the Inventor in Alva, Fla. in February, 2004, of *Hibiscus rosa-sinensis* 'Cajun Wind', disclosed in U.S. Plant Pat. No. 17,589, as the female, or seed, parent with a proprietary selection of *Hibiscus rosa-sinensis* identified as code number YB-2541, not patented, as the male, or pollen, parent. The new *Hibiscus* was discovered and selected by the Inventor as a flowering plant within the progeny of the stated cross-pollination in a controlled greenhouse environment in Alva, Fla. on Sep. 7, 2005.

Asexual reproduction of the new *Hibiscus* by vegetative terminal cuttings in a controlled greenhouse environment in Alva, Fla. since February, 2006, has shown that the unique features of this new *Hibiscus* are stable and reproduced true to type in successive generations.

SUMMARY OF THE INVENTION

Plants of the new *Hibiscus* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Red Nalu'. These characteristics in combination distinguish 'Red Nalu' as a new and distinct cultivar of *Hibiscus:*

1. Compact, upright, outwardly spreading and dense plant habit that is appropriate for container production.
2. Glossy dark green-colored leaves.
3. Uniform, freely and early flowering habit.
4. Large dark red-colored flowers with burgundy-colored centers.
5. Good postproduction and garden performance.

Plants of the new *Hibiscus* can be compared to plants of the female parent, 'Cajun Wind'. Plants of the new *Hibiscus* differ from plants of 'Cajun Wind' in the following characteristics:

1. Plants of the new *Hibiscus* are more outwardly spreading than and not as upright as plants of 'Cajun Wind'.
2. Plants of the new *Hibiscus* and 'Cajun Wind' differ in flower color as plants of 'Cajun Wind' have lighter red-colored flowers.

Plants of the new *Hibiscus* can be compared to plants of the male parent selection. Plants of the new *Hibiscus* differ from plants of the male parent selection in the following characteristics:

1. Plants of the new *Hibiscus* have smaller flowers than plants of the male parent selection.
2. Plants of the new *Hibiscus* and the male parent selection differ in flower color as plants of the male parent selection have dark pink-colored flowers.

Plants of the new *Hibiscus* can be compared to plants of the *Hibiscus rosa-sinensis* 'Baja Breeze', disclosed in U.S. Plant Pat. No. 17,607. In side-by-side comparisons conducted in Alva, Fla., plants of the new *Hibiscus* differed from plants of 'Baja Breeze' in the following characteristics:

1. Plants of the new *Hibiscus* were more vigorous than plants of 'Baja Breeze'.
2. Flowers of plants of the new *Hibiscus* and 'Baja Breeze' differed in flower color as plants of 'Baja Breeze' had lighter red-colored flowers.
3. Plants of the new *Hibiscus* had better garden performance than plants of 'Baja Breeze'.

BRIEF DESCRIPTION OF THE PHOTOGRAPHS

The accompanying colored photographs illustrate the overall appearance of the new *Hibiscus,* showing the colors as true as it is reasonably possible to obtain in colored reproductions of this type. Colors in the photographs may differ slightly from the color values cited in the detailed botanical description which accurately describe the colors of the new *Hibiscus*.

The photograph at the bottom of the sheet comprises a side perspective view of typical flowering plants of 'Red Nalu' grown in a container.

The photograph at the top of the sheet comprises a close-up view of a typical flower of 'Red Nalu'.

DETAILED BOTANICAL DESCRIPTION

The aforementioned photographs and following observations, measurements and values describe plants grown in Bonsall, Calif. in one-gallon containers in polyethylene-covered greenhouses during the spring under conditions which closely approximate commercial production. During the production of the plants, day temperatures ranged from about 18° C. to about 38° C. and night temperatures ranged from about 16° C. to about 21° C. Plants had been growing for 18 weeks when the photographs and the description were taken. In the description, color references are made to The Royal Horticultural Society Colour Chart, 2001 Edition, except where general terms of ordinary dictionary significance are used.

Botanical classification: *Hibiscus rosa-sinensis* 'Red Nalu'.

Parentage:

*Female, or seed, parent.*—*Hibiscus rosa-sinensis* 'Cajun Wind', disclosed in U.S. Plant Pat. No. 17,589.

*Male or pollen parent.*—Proprietary selection of *Hibiscus rosa-sinensis* identified as code number YB-2541, not patented.

Propagation:

*Type.*—By vegetative terminal cuttings.

*Time to initiate roots.*—About 10 days at temperatures of 24° C.

*Time to develop roots.*—About four weeks at temperatures of 24° C.

*Root description.*—Thick, fibrous; white in color.

*Rooting habit.*—Moderate branching; moderately dense.

Plant description:

*Plant form and growth habit.*—Perennial, evergreen, upright, outwardly spreading and dense. Moderately vigorous growth habit.

*Branching habit.*—Freely branching, usually about four to five lateral branches develop.

*Plant height.*—About 40 cm.

*Plant diameter* (*area of spread*).—About 35 cm.

Lateral branch description:

*Length.*—About 28 cm.

*Diameter.*—About 5 mm.

*Internode length.*—About 2.8 cm.

*Texture.*—Immature, sparsely pubescent; mature, woody and rough.

*Color, immature.*—Close to 144A.

*Color, mature.*—Close to 199A to 199B.

Foliage description:

*Arrangement.*—Alternate, single; numerous; symmetrical.

*Length.*—About 9.3 cm.

*Width.*—About 6.4 cm.

*Shape.*—Ovate.

*Apex.*—Acuminate.

*Base.*—Obtuse.

*Margin.*—Broadly serrate to crenate.

*Texture, upper and lower surfaces.*—Smooth, glabrous; leathery and tough.

*Luster, upper surface.*—Glossy.

*Luster, lower surface.*—Somewhat glossy.

*Venation pattern.*—Pinnate; arcuate.

*Color.*—Developing leaves, upper and lower surfaces: Close to 146A. Fully expanded leaves, upper surface: Close to 137A; venation, close to 146A. Fully expanded leaves, lower surface: Close to 146A; venation, close to 146C.

*Petiole.*—Length: About 4.7 cm. Diameter: About 2.5 mm. Texture, upper and lower surfaces: Slightly pubescent. Color, upper and lower surfaces: Close to 146A.

Flower description:

*Flower arrangement.*—Flowers arranged singly at terminal leaf axils. Uniform and freely flowering habit with usually about twelve flower buds and/or open flowers per plant at one time. Flowers face upright to outwardly.

*Flower appearance.*—Rounded, dark red-colored flowers with burgundy-colored centers. Flowers are open for one or two days. Flowers not persistent.

*Natural flowering season.*—Usually spring and summer or during periods of warm weather; plants flower year-round in the greenhouse.

*Flower diameter.*—About 12.7 cm.

*Flower length* (*height*).—About 7.6 cm.

*Flower bud.*—Resistance to abscission during shipping: Plants of the new *Hibiscus* have been observed to resist flower bud drop when stored in a closed box for five days at 13° C. Rate of opening: About five to seven days depending on temperatures. Length: About 4 cm. Diameter: About 1.6 cm. Shape: Ovate. Color: Close to 185B.

*Petals.*—Arrangement: Corolla consists of five petals that are fused at base; petals imbricate. Length: About 7.6 cm. Width: About 5.8 cm. Shape: Obovate. Apex: Rounded. Base: Attenuate. Margin: Entire; slightly sinuate. Texture: Smooth, glabrous; velvety; veins prominent on the lower surface. Color: When opening, upper surface: Close to 45A. When opening, lower surface: Close to 46C. Fully opened, upper surface: Close to 45B; towards the base, darker than 46A. Color does not fade with development. Fully opened, lower surface: Close to 45D. Color does not fade with development.

*Sepals.*—Appearance: Five sepals fused into a tubular star-shaped calyx. Length: About 1.5 cm. Width: About 1.1 cm. Shape: Elliptical. Apex: Acute. Margin: Entire. Texture, upper and lower surfaces: Slightly pubescent. Color, upper surface: Close to 146D. Color, lower surface: Close to 146C.

*Bracts.*—Appearance: About six fused at base. Length: About 1.6 cm. Width: About 3 mm. Shape: Lanceolate. Apex: Acute. Margin: Entire. Texture, upper surface: Smooth, glabrous. Texture, lower surface: Sparsely pubescent. Color, upper and lower surfaces: Close to N137B.

*Peduncles.*—Length: About 6.5 cm. Diameter: About 3 mm. Angle: About 45° from the lateral branch axis.

Strength: Strong, flexible. Texture: Sparsely pubescent. Color: Close to 146B.

*Reproductive organs.*—Androecium: Stamen number: Numerous, about 88. Filament length: About 5 mm. Filament color: Close to 50A. Anther shape: Oval. Anther length: About 1 mm. Anther color: Close to 50A. Amount of pollen: Scarce. Pollen color: Close to 21A. Gynoecium: Pistil length: About 8.8 cm. Style length: About 7.2 cm. Style texture: Smooth, waxy. Style color: Close to 157B. Stigma appearance: Five-parted, rounded. Stigma color: Close to 53A. Ovary color: Close to 160B.

*Seed/fruit.*—Seed and fruit production has not been observed.

Garden performance: Plants of the new *Hibiscus* have been observed to have good garden performance and to tolerate wind, rain and temperatures from about 0° C. to about 38° C.

Pathogen/pest resistance: Plants of the new *Hibiscus* grown under Florida production conditions have not been shown to be susceptible to pathogens common to *Hibiscus* such as Pseudomonas, Pythium and Phytophthora. Plants of the new *Hibiscus* have not been observed to be tolerant to pests and other pathogens.

It is claimed:

1. A new and distinct *Hibiscus* plant named 'Red Nalu' as illustrated and described.

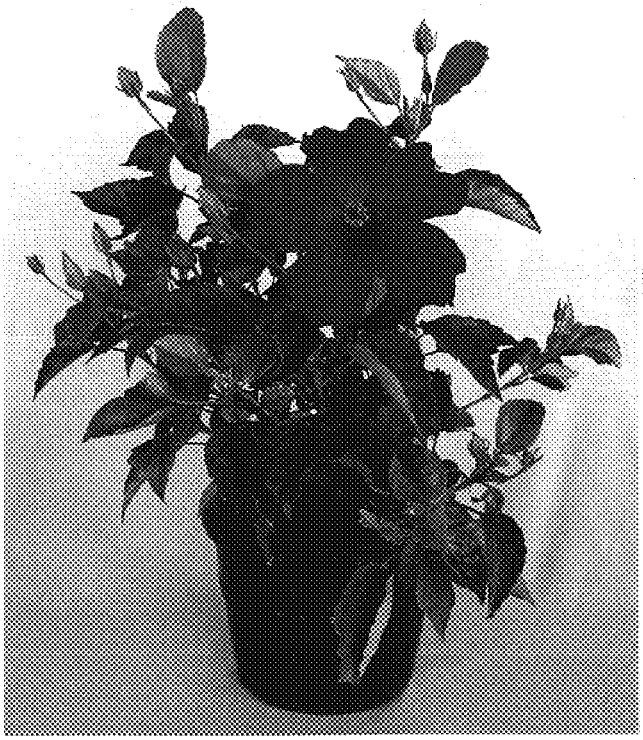
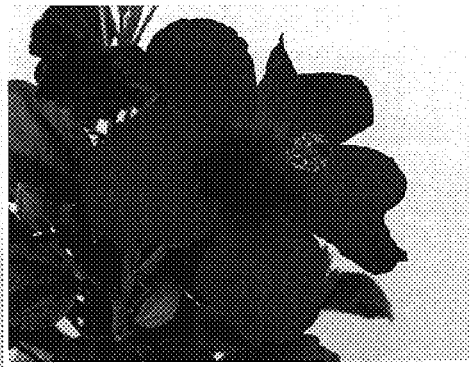

* * * * *